United States Patent [19]

Chang et al.

[11] Patent Number: 4,892,578

[45] Date of Patent: Jan. 9, 1990

[54] PHENYLMETHYL-4,4-DIMETHYL-3-ISOXAZOLIDINONE PLANT REGULATORS

[75] Inventors: Jun H. Chang, Princeton Junction; Jonathan S. Baum, Pennington, both of N.J.

[73] Assignee: FMC Corporation, Philadelphia, Pa.

[21] Appl. No.: 118,390

[22] Filed: Nov. 6, 1987

[51] Int. Cl.$^4$ .................. A01N 43/80; A01N 43/42; C07D 261/04; C07D 413/12

[52] U.S. Cl. .................. 71/94; 71/88; 71/95; 71/92; 548/242; 548/243; 546/84; 546/113; 546/275; 544/137; 544/350; 544/405

[58] Field of Search ............... 71/88, 95, 94; 548/243, 548/242; 546/84

[56] References Cited

U.S. PATENT DOCUMENTS

| | | | |
|---|---|---|---|
| 4,405,357 | 9/1983 | Chang | 71/88 |
| 4,552,585 | 11/1985 | Chang | 71/88 |
| 4,692,182 | 9/1987 | Chang | 71/88 |
| 4,826,527 | 5/1989 | Chang et al. | 71/88 |

Primary Examiner—Mukund J. Shah
Assistant Examiner—E Bernhardt
Attorney, Agent, or Firm—Robert L. Andersen; H. Robinson Erlelt

[57] ABSTRACT

Novel 2-[(4-substituted phenyl)methyl]-4,4-dimethyl-3-isoxazolidinone plant regulators of the following structural formula

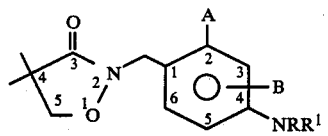

or an agriculturally acceptable salt thereof, agricultural compositions thereof and a method for regulation growth and development of plant growth therewith are disclosed and exemplified.

3 Claims, No Drawings

PHENYLMETHYL-4,4-DIMETHYL-3-ISOXAZOLIDINONE PLANT REGULATORS

This invention relates to heterocyclic organic chemical compounds which contain an isoxazolidinone nucleus and exhibit plant regulator activity. More specifically, the compounds, agricultural compositions, and method of use of this invention utilize certain 2-[(4-substituted phenyl)methyl]-4,4-dimethyl-3-isoxazolidinones as the active ingredient.

U.S. Pat. Nos. 4,405,357 and 4,552,585 describe herbicidal 2-[(substituted phenyl)methyl]-4,4-dimethyl-3-isoxazolidinones in which the substituents on the 2-phenylmethyl group include hydrogen, halogen, alkyl, phenyl, haloalkyl, nitro, alkoxy, methylenedioxy, cyano, and amido. U.S. Pat. No. 4,692,182 issued Sept. 8, 1987 describes herbicidal 2-[(substituted phenyl)methyl]-4,4-dimethyl-3-isoxazolidinones in which one substituent on the phenyl ring is a substituted hydrazine group.

The present invention relates to chemical compounds which beneficially modify growth and development of plants. Such compounds are hereinafter referred to as plant growth regulators or simply plant regulators. Unlike broad spectrum herbicides, which kill desirable plants as well as weeds, or selective herbicides which minimize effect on desired plants but kill weeds growing adjacent thereto, plant regulators, when applied in the proper manner, exert beneficial effects by selectively modifying the normal growth and development of desirable plants such as agricultural crops.

Beneficial effects from such modification include increasing the yield of fruit, seeds, fiber, or other plant products, increasing the nutritional value of food products derived from the plants, facilitating harvesting of the plant product, or increasing the products' storage life. Plant growth and development modifications leading to such effects include, but are not limited to: root initiation; set, development, ripening and abscission of fruits; modification of plants size and shape; suppression of lodging; control of axillary buds and lateral shoots; metabolism regulation, including senescence and auxin transport inhibition; breaking or enforcing dormancy in seeds, buds, and storage organs; promotion or delay of flowering; defoliation; desiccation; and growth promotion under stress.

Sometimes a compound displays herbicidal and plant growth and development regulation activity depending upon the species of plant, the time of application in the plant growth cycle, the site of application, and the amount of chemical employed, i.e., the application rate. Most of the 2-[(4-substituted phenyl)methyl]-4,4-dimethyl-3-isoxazolidinones of this invention can be made to behave as either herbicides or plant regulators depending upon the way they are used.

The 2-[(4-substituted phenyl)methyl]-4,4-dimethyl-3-isoxazolidinone plant regulators of the present invention are represented by the following structural formula

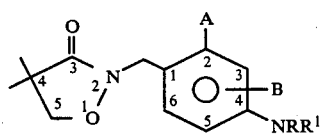

or an agriculturally acceptable salt thereof in which
(A) A is hydrogen or halogen,
B is hydrogen or halogen,
or A and B together form —$C_4H_4$— bridging adjacent carbon atoms;
R is hydrogen or alkyl;

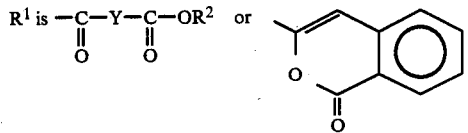

$R^2$ is hydrogen, methyl, diphenylmethyl or an agriculturally acceptable cation; and
Y is
(a) lower alkylene or lower alkenylene which may be substituted with halogen or phenyl,
(b) ortho-cyclohexylene or ortho-cyclohexenylene which may be substituted with methyl,
(c) ortho-bicycloalkylene of 7 or 8 carbon atoms,
(d) ortho-oxabicycloalkenylene of 6 or 7 carbon atoms,
(e) ortho-phenylene which may be substituted with lower alkyl, halogen, nitro, a group of formula I

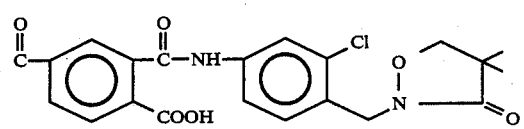

or with carboxyl and a group of formula II

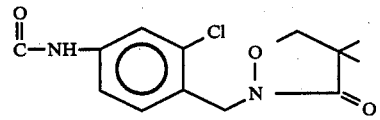

(f) ortho-naphthalene,
(g) ortho-phenylmethylene,
(h) ortho-pyridinylene, or
(i) ortho-pyrazinylene, or
(B) A and B are defined above and $NRR^1$ comprises (2-hydroxyphenyl)methylimino, (4-halo-2-hydroxyphenyl)-methylimino, or (thien-2-yl)methylimino, or phthalidylidenylamino, or a group of the formula

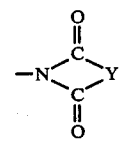

in which Y is as defined above or is —$CH_2OCH_2$—

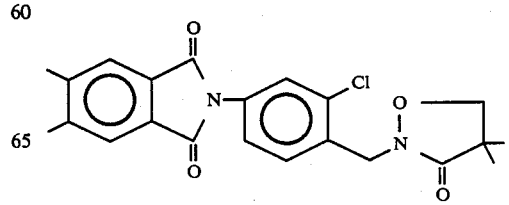

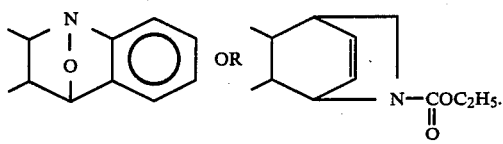

In the aforesaid description and wherever the terms appear hereinafter, unless a contrary intent is clearly expressed, "halo" and "halogen" mean fluorine, chlorine or bromine; the term "lower" modifying an alkyl or other hydrocarbon group implies a straight or branched hydrocarbon chain of 1-6, preferably 1-4, carbon atoms; "halo" coupled with another term means one or more hydrogen atoms has been replaced by halogen; and "cyclo-alkyl" means a saturated hydrocarbon ring containing 3-8 carbon atoms.

The compounds of this invention may be prepared by the methods disclosed in U.S. Pat. No. 4,552,585 modified by the methods disclosed in Cava et al., Org. Syn. Coll., Vol. V, 944-946, both incorporated herein by reference, and by methods well known to those skilled in the art.

Specific examples of the foregoing compounds, together with compound numbers, and characterizing data are set forth in Table I below. In the characterizing data column, data in parentheses are melting points in °C.

TABLE I

| Cmpd No. | Name | Characterizing Data (°C.) |
|---|---|---|
| 10 | 2-[[2-chloro-4-[(2-carboxyethyl)carbonylamino]phenyl]methyl]-4,4-dimethyl-3-isoxazolidinone | (194-198) |
| 11 | Z-2-[[2-chloro-4-[(2-carboxyethenyl)carbonylamino]phenyl]methyl]-4,4-dimethyl-3-isoxazolidinone | (188-190) |
| 12 | 2-[[2-chloro-4-[(1-bromo-2-carboxyethenyl)-carbonylamino]phenyl]methyl]-4,4-dimethyl-3-isoxazolidinone<br>2-[[2-chloro-4-[(2-bromo-2-carboxyethenyl)-carbonylamino]phenyl]methyl]-4,4-dimethyl-3-isoxazolidinone | (135-138)<br>isomeric mixture |
| 13 | 2-[[2-chloro-4-[(1,2-dichloro-2-carboxyethenyl)carbonylamino]phenyl]methyl]-4,4-dimethyl-3-isoxazolidinone | (149-152) |
| 14 | cis-2-[[2-chloro-4-[(2-carboxy-1-phenylethenyl)carbonylamino]phenyl]methyl]-4,4-dimethyl-3-isoxazolidinone<br>cis-2-[[2-chloro-4-[(2-carboxy-2-phenylethenyl)carbonylamino]phenyl]methyl] 4,4-dimethyl-3-isoxazolidinone | (185-187)<br>isomeric mixture |
| 15 | 2-[[2-chloro-4-[(3-carboxypropyl)carbonylamino]phenyl]methyl]-4,4-dimethyl-3-isoxazolidinone | (160-162) |
| 16 | 2-[[2-chloro-4-[(2-carboxypropyl)carbonylamino]phenyl]methyl]-4,4-dimethyl-3-isoxazolidinone<br>2-[[2-chloro-4-[(2-carboxy-1-methylethyl)-carbonylamino]phenyl]methyl]-4,4-dimethyl-3-isoxazolidinone | (150-160)<br>isomeric mixture |
| 17 | 2-[[2-chloro-4-[(2-carboxyprop-2-enyl)-carbonylamino]phenyl]methyl]-4,4-dimethyl-3-isoxazolidinone | (160-163) |
| 18 | cis-2-[[2-chloro-4-[(2-carboxycyclohexyl)-carbonylamino]phenyl]methyl]-4,4-dimethyl-3-isoxazolidinone | (196-198) |
| 19 | cis-2-[[2-chloro-4-[(2-carboxy-4-methylcyclohexyl)carbonylamino]phenyl]methyl]-4,4-dimethyl-3-isoxazolidinone<br>cis-2-[[2-chloro-4-[(2-carboxy-5-methylcyclohexyl)carbonylamino]phenyl]methyl]-4,4-dimethyl-3-isoxazolidinone | (135-140)<br>isomeric mixture |
| 20 | 2-[[4-[(2-carboxycyclohex-1-enyl)carbonylamino]phenyl]methyl]-4,4-dimethyl-3-isoxazolidinone | (150-152) |
| 21 | 2-[[2-chloro-4-[(2-carboxycyclohex-1-enyl)-carbonylamino]phenyl]methyl]-4,4-dimethyl-3-isoxazolidinone | (154-156) |
| 22 | 2-[[2-bromo-4-[(2-carboxycyclohex-1-enyl)-carbonylamino]phenyl]methyl]-4,4-dimethyl-3-isoxazolidinone | (149-151) |
| 23 | 2-[[2-fluoro-4-[(2-carboxycyclohex-1-enyl)-carbonylamino]phenyl]methyl]-4,4-dimethyl-3-isoxazolidinone | (163, dec) |
| 24 | 2-[[2-chloro-4-[(2-carboxycyclohex-1-enyl)-carbonylamino]-5-fluorophenyl]methyl]-4,4-dimethyl-3-isoxazolidinone | (123-125) |
| 25 | 2-[[4-[(2-carboxycyclohex-2-enyl)carbonylamino]phenyl]methyl]-4,4-dimethyl-3-isoxazolidinone<br>2-[[4-[(2-carboxycyclohex-6-enyl)carbonylamino]phenyl]methyl]-4,4-dimethyl-3-isoxazolidinone | (183-185)<br>isomeric mixture |

TABLE I-continued

| Cmpd No. | Name | Characterizing Data (°C.) |
|---|---|---|
| 26 | 2-[[2-chloro-4-[(2-carboxycyclohex-2-enyl)-carbonylamino]phenyl]methyl]-4,4-dimethyl-3-isoxazolidinone<br>2-[[2-chloro-4-[(2-carboxycyclohex-6-enyl)-carbonylamino]phenyl]methyl]-4,4-dimethyl-3-isoxazolidinone | (184–186)<br>isomeric mixture |
| 27 | cis-2-[[2-chloro-4-[(2-carboxycyclohex-4-enyl)carbonylamino]phenyl]methyl-4,4-dimethyl-3-isoxazolidinone | (208–210) |
| 28 | cis-2-[[4-[(2-carboxy-4-methylcyclohex-4-enyl)carbonylamino]phenyl]methyl]-4,4-dimethyl-3-isoxazolidinone<br>cis-2-[[4-[(2-carboxy-5-methylcyclohex-4-enyl)carbonylamino]phenyl]methyl]-4,4-dimethyl-3-isoxazolidinone | (189–190)<br>isomeric mixture |
| 29 | cis-2-[[2-chloro-4-[(2-carboxy-4-methyl-cyclohex-4-enyl)carbonylamino]phenyl]-methyl]-4,4-dimethyl-3-isoxazolidinone<br>cis-2-[[2-chloro-4-[(2-carboxy-5-methyl-cyclohex-4-enyl)carbonylamino]phenyl]-methyl]-4,4-dimethyl-3-isoxazolidinone | (177–179)<br>isomeric mixture |
| 30 | cis,endo-2-[[2-chloro-4-[(3-carboxybi-cyclo[2.2.1]hept-5-enyl)-2-carbonyl-amino]phenyl]methyl-4,4-dimethyl-3-isoxazolidinone | (172–174) |
| 31 | cis,endo-2-[[2-chloro-4-[(3-carboxy-bicyclo[2.2.2]oct-5-enyl)-2-carbonylamino]phenyl]methyl]-4,4-dimethyl-3-isoxazolidinone | (148–150) |
| 32 | cis,endo-2-[[2-chloro-4-[(3-carboxy-7-oxa-bicyclo[2.2.1]hept-5-enyl)-2-carbonylamino]-phenyl]methyl]-4,4-dimethyl-3-isoxazolidinone | (123–125) |
| 34 | 2-[[4-[(2-carboxyphenyl)carbonylamino]-phenyl]methyl]-4,4-dimethyl-3-isoxazolidinone | (152–154) |
| 35 | 2-[[2-chloro-4-[(2-carboxyphenyl)carbonyl-amino]phenyl]methyl]-4,4-dimethyl-3-isoxazolidinone | (172, dec) |
| 36 | 2-[[2-bromo-4-[(2-carboxyphenyl)carbonyl-amino]phenyl]methyl]-4,4-dimethyl-3-isoxazolidinone | (177, dec) |
| 37 | 2-[[2-fluoro-4-[(2-carboxyphenyl)carbonyl-amino]phenyl]methyl]-4,4-dimethyl-3-isoxazolidinone | (142, dec) |
| 38 | 2-[[2-iodo-4-[(2-carboxyphenyl)carbonyl-amino]phenyl]methyl]-4,4-dimethyl-3-isoxazolidinone | (163–165) |
| 39 | 2-[[2,5-dichloro-4-[(2-carboxyphenyl)-carbonylamino]phenyl]methyl]-4,4-dimethyl-3-isoxazolidinone | (155–158) |
| 40 | 2-[[2-chloro-4-[(2-carboxyphenyl)carbonyl-amino]-5-fluorophenyl]methyl]-4,4-dimethyl-3-isoxazolidinone | (170–173) |
| 41 | 2-[[4-[(2-carboxyphenyl)carbonylamino]-naphth-1-yl]methyl]-4,4-dimethyl-3-isoxazolidinone | (185–187) |
| 42 | 2-[[2-chloro-4-[(2-carboxy-6-chlorophenyl)carbonylamino]phenyl]methyl]-4,4-dimethyl-3-isoxazolidinone | (117–120) |
| 43 | 2-[[4-[(2-carboxy-4-chlorophenyl)carbonyl-amino]phenyl]methyl]-4,4-dimethyl-3-isoxazolidinone<br>2-[[4-[(2-carboxy-5-chlorophenyl)carbonyl-amino]phenyl]methyl]-4,4-dimethyl-3-isoxazolidinone | (170–172)<br>isomeric mixture |
| 44 | 2-[[2-chloro-4-[(2-carboxy-4-chlorophenyl)-carbonylamino]phenyl]methyl]-4,4-dimethyl-3-isoxazolidinone<br>2-[[2-chloro-4-[(2-carboxy-5-chlorophenyl)-carbonylamino]phenyl]methyl]-4,4-dimethyl-3-isoxazolidinone | (172–174)<br>isomeric mixture |
| 45 | 2-[[2-chloro-4-[(2-carboxy-4,5-dichloro-phenyl)carbonylamino]phenyl]methyl]-4,4-dimethyl-3-isoxazolidinone | (184–186) |
| 46 | 2-[[2-chloro-4-[(2-carboxy-3,4,5,6-tetra-chlorophenyl)carbonylamino]phenyl]methyl]-4,4-dimethyl-3-isoxazolidinone | (190–192) |
| 47 | 2-[[2-chloro-4-[(2-carboxy-3,4,5,6-tetra-bromophenyl)carbonylamino]phenyl]methyl]-4,4-dimethyl-3-isoxazolidinone | (268–270) |
| 48 | 2-[[4-[(2-carboxy-4-methylphenyl)carbonyl-amino]phenyl]methyl]-4,4-dimethyl-3-isoxazolidinone | (157–159)<br>isomeric mixture |

TABLE I-continued

| Cmpd No. | Name | Characterizing Data (°C.) |
|---|---|---|
|  | 2-[[4-[(2-carboxy-5-methylphenyl)carbonyl-amino]phenyl]methyl-4,4-dimethyl-3-isoxa-zolidinone |  |
| 49 | 2-[[2-chloro-4-[(2-carboxy-4-methylphenyl)-carbonylamino]phenyl]methyl]-4,4-dimethyl-3-isoxazolidinone | (181–183) isomeric mixture |
|  | 2-[[2-chloro-4-[(2-carboxy-5-methylphenyl)carbonylamino]phenyl]methyl]-4,4-dimethyl-3-isoxazolidinone |  |
| 50 | 2-[[2-chloro-4-[(2-carboxy-4-nitrophenyl)-carbonylamino]phenyl]methyl]-4,4-dimethyl-3-isoxazolidinone | (123–126) isomeric mixture |
|  | 2-[[2-chloro-4-[(2-carboxy-5-nitrophenyl)-carbonylamino]phenyl]methyl]-4,4-dimethyl-3-isoxazolidinone |  |
| 51 | 4,4'-dicarboxy-3,3'-bis[[3-chloro-4-(4,4-dimethyl-3-isoxazolidinone-2-ylmethyl)phenyl]-aminocarbonyl]benzophenone | (130, dec) isomeric mixture |
|  | 3,4'-dicarboxy-3',4-bis[[3-chloro-4-(4,4-dimethyl-3-isoxazolidinone-2-ylmethyl)phenyl]-aminocarbonyl]benzophenone |  |
| 52 | 4,6-dicarboxy-bis[[3-chloro-4-(4,4-dimethyl-3-isoxazolidinone-2-ylmethyl)phenyl]amino-carbonyl]-1,3-phenylene | (262–265) isomeric mixture |
|  | 2,5-dicarboxy-bis[[3-chloro-4-(4,4-dimethyl-isoxazolidinone-2-ylmethyl)phenyl]amino-carbonyl]-1,4-phenylene |  |
| 53 | 2-[[4-[(3-carboxynaphth-2-yl)carbonylamino]-phenyl]methyl]-4,4-dimethyl-3-isoxazolidinone | (247–249) |
| 54 | 2-[[2-chloro-4-[(3-carboxynaphth-2-yl)-carbonylamino]phenyl]methyl]-4,4-dimethyl-3-isoxazolidinone | (182–184) |
| 55 | 2-[[2-chloro-4-[N—methyl-(2-carboxyphenyl)-carbonylamino]phenyl]methyl]-4,4-dimethyl-3-isoxazolidinone | (72–82) |
| 56 | 2-[[2-chloro-4-[N—ethyl-(2-carbomethoxy-phenyl)carbonylamino]phenyl]methyl]-4,4-dimethyl-3-isoxazolidinone | gum |
| 57 | 2-[[2-chloro-4-[N—propyl-(2-carbomethoxy-phenyl)carbonylamino]phenyl]methyl]-4,4-dimethyl-3-isoxazolidinone | oil |
| 58 | 2-[[2-chloro-4-[N—(2,2-dimethylpropyl)-(2-carbomethoxyphenyl)carbonylamino]phenyl]-methyl]-4,4-dimethyl-3-isoxazolidinone | foamy solid |
| 59 | 2-[[4-[(2-carboxyphenylmethyl)carbonylamino]-phenyl]methyl]-4,4-dimethyl-3-isoxazolidinone | (164–166) |
| 60 | 2-[[2-chloro-4-[(2-carboxyphenylmethyl)-carbonylamino]phenyl]methyl]-4,4-dimethyl-3-isoxazolidinone | (194–195) |
| 61 | 2-[[4-[(3-carboxy-2-pyridinyl)carbonylamino]-phenyl]methyl]-4,4-dimethyl-3-isoxazolidinone | (123–125) |
| 62 | 2-[[2-chloro-4-[(3-carboxy-2-pyridinyl)-carbonylamino]phenyl]methyl]-4,4-dimethyl-3-isoxazolidinone | (94–96) |
| 63 | 2-[[2-chloro-4-[(3-carboxy-4-pyridinyl)-carbonylamino]phenyl]methyl]-4,4-dimethyl-3-isoxazolidinone | (170–172) |
| 64 | 2-[[2-chloro-4-[ (3-carboxy-4-pyridinyl)-carbonylamino]phenyl]methyl]-4,4-dimethyl-3-isoxazolidinone, 1-methylethylamine salt | (130–132) |
| 65 | 2-[[2-chloro-4-[(3-carbodiphenylmethoxy-4-pyridinyl)carbonylamino]phenyl]methyl]-4,4-dimethyl-3-isoxazolidinone | (171–173) |
| 66 | 2-[[2-chloro-4-[(3-carboxy-2-pyrazinyl)-carbonylamino]phenyl]methyl]-4,4-dimethyl-3-isoxazolidinone | (171–173) |
| 67 | 2-[[4-[(1H—2-benzopyran-1-one-3-yl)amino]-phenyl]methyl]-4,4-dimethyl-3-isoxazolidinone | (175–178) |
| 68 | 2-[[2-chloro-4-[(1H—2-benzopyran-1-one-3-yl)amino]phenyl]methyl]-4,4-dimethyl-3-isoxazol-idinone | (184–186) |
| 71 | 2-[[2-chloro-4-[(2-hydroxyphenyl)methyl-imino]phenyl]methyl]-4,4-dimethyl-3-isoxazol-idinone | (105–107) |
| 72 | 2-[[2-chloro-4-[(5-chloro-2-hydroxyphenyl)-methylimino]phenyl]methyl]-4,4-dimethyl-3-isoxazolidinone | (112–114) |
| 73 | 2-[[4-[(thien-2-yl)methylimino]phenyl]-methyl]-4,4-dimethyl-3-isoxazolidinone | (78–81) |
| 74 | 2-[[2-chloro-4-[(thien-2-yl)methylimino]-phenyl]methyl]-4,4-dimethyl-3-isoxazolidinone | oil |

TABLE I-continued

| Cmpd No. | Name | Characterizing Data (°C.) |
|---|---|---|
| 75 | 2-[[2-chloro-4-(phthalidylidenylamino)phenyl]-methyl]-4,4-dimethyl-3-isoxazolidinone | (122–126) |
| 76 | 2-[(2-chloro-4-succinimidophenyl)methyl]-4,4-dimethyl-3-isoxazolidinone | (175–176) |
| 77 | 2-[[2-chloro-4-(3-methylsuccinimido)phenyl]-methyl]-4,4-dimethyl-3-isoxazolidinone | (144–146) |
| 78 | 2-[[2-chloro-4-(hexahydrophthalimido)phenyl]-methyl]-4,4-dimethyl-3-isoxazolidinone | (97–99) |
| 79 | cis-2-[[2-chloro-4-(4-methylhexahydrophthal-imido)phenyl]methyl]-4,4-dimethyl-3-isoxazol-idinone | oil |
| 80 | 2-[(2-chloro-4-glutarimidophenyl)methyl]-4,4-dimethyl-3-isoxazolidinone | (195–197) |
| 81 | 2-[[2-chloro-4-(4,4-dimethylglutarimido)-phenyl]methyl]-4,4-dimethyl-3-isoxazolidinone | (160–162) |
| 82 | 2-[[2-chloro-4-[(1,4-oxazin-3,5-dione-4-yl)-phenyl]methyl]-4,4-dimethyl-3-isoxazolidinone | (175–178) |
| 83 | 2-[(2-chloro-4-maleimidophenyl)methyl]-4,4-dimethyl-3-isoxazolidinone | (98–102) |
| 84 | 2-[[2-chloro-4-(3-bromomaleimido)phenyl]-methyl]-4,4-dimethyl-3-isoxazolidinone | (110–111) |
| 85 | 2-[[2-chloro-4-(3,4-dichloromaleimido)-phenyl]methyl]-4,4-dimethyl-3-isoxazolidinone | (142–145) |
| 86 | 2-[[2-chloro-4-(3-methylmaleimido)phenyl]-methyl]-4,4-dimethyl-3-isoxazolidinone | gum |
| 87 | 2-[[2-chloro-4-(3-phenylmaleimido)phenyl]-methyl]-4,4-dimethyl-3-isoxazolidinone | (93–96) |
| 88 | 2-[[2-chloro-4-(3,4,5,6-tetrahydrophthal-imido)phenyl]methyl]-4,4-dimethyl-3-isoxazolidinone | (102–104) |
| 89 | 2-[[2-fluoro-4-(3,4,5,6-tetrahydrophthal-imido)phenyl]methyl]-4,4-dimethyl-3-isoxazolidinone | (92–94) |
| 90 | 2-[[2-iodo-4-(3,4,5,6-tetrahydrophthal-imido)phenyl]methyl]-4,4-dimethyl-3-isoxa-zolidinone | (139–141) |
| 91 | 2-[[2-chloro-5-fluoro-4-(3,4,5,6-tetrahydro-phthalimido)phenyl]methyl]-4,4-dimethyl-3-isoxazolidinone | oil |
| 92 | 2-[[4-(2,3,4,5-tetrahydrophthalimido)phenyl]-methyl]-4,4-dimethyl-3-isoxazolidinone | (121–123) |
| 93 | 2-[[2-chloro-4-(2,3,4,5-tetrahydrophthal-imido)phenyl]methyl]-4,4-dimethyl-3-isoxa-zolidinone | (134–136) |
| 94 | cis-2-[[2-chloro-4-(1,2,3,6-tetrahydrophthal-imido)phenyl]methyl]-4,4-dimethyl-3-isoxazol-idinone | (114–115) |
| 95 | cis-2-[[4-(4-methyl-1,2,3,6-tetrahydrophthal-imido)phenyl]methyl]-4,4-dimethyl-3-isoxazol-idinone | (86–87) |
| 96 | cis-2-[[2-chloro-4-(4-methyl-1,2,3,6-tetra-hydrophthalimido)phenyl]methyl]-4,4-dimethyl-3-isoxazolidinone | oil |
| 97 | cis,endo-2-[[2-chloro-4-[bicyclo[2.2.1]-5-heptenimido]phenyl]methyl]-4,4-dimethyl-3-isxazolidinone | (142–145) |
| 98 | cis,endo-2-[[2-chloro-4-[bicyclo[2.2.2]-5-octenimido]phenyl]methyl]-4,4-dimethyl-3-isoxazolidinone | (164–167) |
| 99 | cis,endo-2-[[2-chloro-4-[7-oxabicyclo[2.2.1]-5-heptenimido]phenyl]methyl]-4,4-dimethyl-3-isoxazolidinone | (96–98) |
| 100 | 2-[(4-phthalimidophenyl)methyl]-4,4-dimethyl-3-isoxazolidinone | (140–142) |
| 101 | 2-[(2-chloro-4-phthalimidophenyl)methyl]-4,4-dimethyl-3-isoxazolidinone | (141–145) |
| 102 | 2-[(2-bromo-4-phthalimidophenyl)methyl]-4,4-dimethyl-3-isoxazolidinone | (158–159) |
| 103 | 2-[(2-fluoro-4-phthalimidophenyl)methyl]-4,4-dimethyl-3-isoxazolidinone | (119–120) |
| 104 | 2-[(2-iodo-4-phthalimidophenyl)methyl]-4,4-dimethyl-3-isoxazolidinone | (157–159) |
| 105 | 2-[(2,3-dichloro-4-phthalimidophenyl)-methyl]-4,4-dimethyl-3-isoxazolidinone | (160–162) |
| 106 | 2-[(2,5-dichloro-4-phthalimidophenyl)-methyl]-4,4-dimethyl-3-isoxazolidinone | (162–164) |
| 107 | 2-[(2-chloro-5-fluoro-4-phthalimidophenyl)-methyl]-4,4-dimethyl-3-isoxazolidinone | (149–152) |
| 108 | 2-[(4-phthalimidonaphth-1-yl)methyl]-4,4-di-methyl-3-isoxazolidinone | (215–217) |
| 109 | 2-[[2-chloro-4-(3-chlorophthalimido)phenyl]- | |

TABLE I-continued

| Cmpd No. | Name | Characterizing Data (°C.) |
|---|---|---|
| | methyl]-4,4-dimethyl-3-isoxazolidinone | (132–134) |
| 110 | 2-[[4-(4-chlorophthalimido)phenyl]methyl]-4,4-dimethyl-3-isoxazolidinone | (123–125) |
| 111 | 2-[[2-chloro-4-(4-chlorophthalimido)phenyl]-methyl]-4,4-dimethyl-3-isoxazolidinone | (65–68) |
| 112 | 2-[[2-chloro-4-(4,5-dichlorophthalimido)-phenyl]methyl]-4,4-dimethyl-3-isoxazolidinone | (175–178) |
| 113 | 2-[[2-chloro-4-(3,4,5,6-tetrachlorophthal-imido)phenyl]methyl]-4,4-dimethyl-3-isoxazolidinone | (187–189) |
| 114 | 2-[[2-chloro-4-(3,4,5,6-tetrabromophthal-imido)phenyl]methyl]-4,4-dimethyl-3-isoxazolidinone | (280–282) |
| 115 | 2-[[4-(4-methylphthalimido)phenyl]methyl]-4,4-dimethyl-3-isoxazolidinone | (161–163) |
| 116 | 2-[[2-chloro-4-(4-methylphthalimido(phenyl]-methyl]-4,4-dimethyl-3-isoxazolidinone | (89–91) |
| 117 | 2-[[2-chloro-4-(3-nitrophthalimido)phenyl]-methyl]-4,4-dimethyl-3-isoxazolidinone | (165–167) |
| 118 | 2-[[2-chloro-4-(4-nitrophthalimido)phenyl]-methyl]-4,4-dimethyl-3-isoxazolidinone | (128–130) |
| 119 | 2-[[4-(2,3-naphthalimido)phenyl]methyl]-4,4-dimethyl-3-isoxazolidinone | (248–250) |
| 120 | 2-[[2-chloro-4-(2,3-naphthalimido)phenyl]-methyl]-4,4-dimethyl-3-isoxazolidinone | (220–222) |
| 121 | 2-[[2-chloro-4-(pyrrolo[3,4-b]pyridine-5,7-dione-6-yl)phenyl]methyl]-4,4-dimethyl-3-isoxazolidinone | (139–141) |
| 122 | 2-[[2-chloro-4-(pyrrolo[3,4-c]pyridine-5,7-dione-6-yl)phenyl]methyl]-4,4-dimethyl-3-isoxazolidinone | (174–177) |
| 123 | 2-[[2-chloro-4-(pyrrolo[3,4-b]pyrazine-5,7-dione-6-yl)phenyl]methyl]-4,4-dimethyl-3-isoxazolidinone | (180–181) |
| 124 | N,N'—bis[3-chloro-4-(4,4-dimethyl-3-isoxazol-idinone-2-ylmethyl)]pyromellitic diimide | (265–267) |
| 125 | cis-2-[[2-chloro-4-(4,9-epoxy-4H—pyrrolidine-[3,4-b]quinoline-1,3-dione-2-yl)phenyl]-methyl]-4,4-dimethyl-3-isoxazolidinone | (129–132) |
| 126 | cis-2-[[2-chloro-4-[5-(ethoxycarbonyl)-4,5-etheno-1H'pyrralidino[3,4-c]piperidine-1,3-dione-2-yl]-4,4-dimethyl-3-isoxazolidinone | (165–167) |

The following examples illustrate the methods for preparing these compounds.

EXAMPLE 1

Synthesis of a mixture of
2-[[2-chloro-4-[(2-carboxy-cyclohex-2-enyl)car-bonylamino]phenyl]methyl]-4,4-dimethyl-3-isoxazolidinone and its isomer
2-[[2-chloro-4-[(2-carboxycyclohex-6-enyl)car-bonylamino]phenyl]methyl]-4,4-dimethyl-3-isoxazolidinone (Compound 26)

Step A:

Synthesis of cyclohexene-2,3-dicarboxylic acid as an intermediate

A stirred solution of 12.0 grams (0.067 mole) of ethyl 2-cyanocyclohex-2-enecarboxylate (prepared by the method of G. Kon and B. Nandi, JCS, 1628–1633 (1933), and 75 ml of aqueous 30% potassium hydroxide in approximately 20 ml of ethanol was heated under reflux for 16 hours. The reaction mixture was cooled and concentrated under reduced pressure to a residue. The residue was cooled in an ice bath, and the pH was adjusted to 2 with sulfuric acid. The resultant precipitate was collected by filtration and was dried to yield 5.0 grams of cyclohexene-2,3-dicarboxylic acid; m.p. 201°–203° C.

Step B:

Synthesis of 2,3,4,5-tetrahydrophthalic anhydride as an intermediate

A stirred solution of 5.0 grams (0.029 mole) of cyclohexene-2,3-dicarboxylic acid in 30 ml of acetic anhydride and 100 ml of acetic acid was heated under reflux for four hours. The reaction mixture was concentrated under reduced pressure to a residual oil. The oil was washed with petroleum ether and evacuated under high vacuum to yield 2.2 grams of 2,3,4,5-tetrahydrophthalic anhydride as a semi-solid.

The IR spectrum was consistent with the proposed structure.

Step C:

Synthesis of a mixture of
2-[[2-chloro-4-[(2-carboxycyclohex-2-enyl)car-bonylamino]phenyl]methyl]-4,4-dimethyl-3-isoxazolidinone and its isomer
2-[[2-chloro-4-[(2-carboxycyclohex-6-enyl)car-bonylamino]-phenyl]methyl]-4,4-dimethyl-3-isoxazolidinone Using a method analogous to that of M. P. Cava et al., supra, a solution of 1.2 grams (0.008 mole) of 2,3,4,5-tetrahydrophthalic anhydride in 50 mL of tetrahydrofuran was stirred, and a solution of 2.0 grams (0.008 mole) of 2-[(4-amino-2-chlorophenyl)methyl]-4,4-dimethyl-3-isoxazolidinone in 50 mL of tetrahydrofuran was added dropwise. Upon completion of addition the reaction mixture was stirred at ambient temperature for four hours. The reaction mixture was concentrated under reduced pressure to a semi-solid residue. The residue was stirred with acetone-petroleum ether, and the resultant solid was collected by filtration to yield 1.3 grams of a mixture of 2-[[2-chloro-4-[(2-carboxycyclohex-2-enyl)carbonylamino]phenyl]methyl]-4,4-dimethyl-3-isoxazolidinone and its isomer 2-[[2-chloro-4-[(2-carboxycyclohex-6-enyl)carbonylamino]phenyl]methyl]-4,4-dimethyl-3-isoxazolidinone; m.p. 184°–186° C.

EXAMPLE 2

Synthesis of
2-[[2-chloro-4-[(2-carboxyphenyl)-carbonylamino]-phenyl]methyl]-4,4-dimethyl-3-isoxazolidinone (Compound 35)

This compound was prepared in a manner analogous to that of Example 1, Step C, using 3.0 grams (0.012 mole) of 2-[(4-amino-2-chlorophenyl)methyl]-4,4-dimethyl-3-isoxazolidinone and 1.8 grams (0.012 mole) of phthalic anhydride in 125 mL of tetrahydrofuran. The reaction mixture was dissolved in 200 mL of methylene chloride and washed with four 50 mL portions of an aqueous 10% hydrochloric acid solution. The organic layer was dried with magnesium sulfate and filtered. The filtrate was concentrated under reduced pressure to a semi-solid residue. The residue was stirred and heated in ethyl acetate-heptane. The resultant solid was collected by filtration and was recrystallized from acetate/hexane to yield 0.5 gram of 2-[[2-chloro-4-[(2-carboxyphenyl)carbonylamino]phenyl]methyl]-4,4-dimethyl-3-isoxazolidinone; m.p. 172° C., dec.

The nmr spectrum was consistent with the proposed structure.

EXAMPLE 3

Synthesis of
2-[[2-chloro-4-[(2-carboxyphenylmethyl)carbonylamino]phenyl]methyl]-4,4-dimethyl-3-isoxazolidinone (Compound 60)

This compound was prepared in a manner analogous to that of Example 1, Step C, using 4.0 grams (0.016 mole) of 2-[(4-amino-2-chlorophenyl)methyl]-4,4-dimethyl-3-isoxazolidinone and 2.6 grams (0.016 mole) of homophthalic anhydride in 150 mL of tetrahydrofuran. The reaction mixture was concentrated under reduced pressure to a residual oil. The oil was dissolved in acetone, and petroleum ether was added. The resultant solid was collected by filtration and was recrystallized from acetone/water to yield 3.9 grams of 2-[[2-chloro-4-[(2-carboxyphenylmethyl)carbonylamino]phenyl]methyl]-4,4-dimethyl-3-isoxazolidinone; m.p. 194°–196° C.

EXAMPLE 4

Synthesis of
2-[[2-chloro-4-[(3-carboxy-2-pyridinyl)carbonylamino]-phenyl]methyl]-4,4-dimethyl-3-isoxazolidinone (Compound 62)

This compound was prepared in a manner analogous to that of Example 1, Step C, using 4.0 grams (0.016 mole) of 2-[(4-amino-2-chlorophenyl)methyl]-4,4-dimethyl-3-isoxazolidinone and 2.3 grams (0.016 mole) of 2,3-pyridinedicarboxylic anhydride in 175 mL of tetrahydrofuran. The reaction mixture was filtered, and the filtrate was concentrated under reduced pressure to a residual oil. The oil was crystallized by dissolving it in ethanol and adding diethyl ether until precipitation occurred. The solid was recrystallized in the same manner to yield 2.2 grams of 2-[[2-chloro-4-[(3-carboxy-2-pyridinyl)carbonylamino]phenyl]methyl]-4,4-dimethyl-3-isoxazolidinone; m.p. 94°–96° C.

EXAMPLE 5

Synthesis of
2-[[2-chloro-4-[(2-hydroxyphenyl)-methylimino]-phenyl]methyl]-4,4-dimethyl-3-isoxazolidinone (Compound 71)

A warmed solution of 0.48 gram (0.004 mole) of salicylaldehyde in 35 mL of ethanol was stirred, and 1.0 gram (0.004 mole) of 2-[(4-amino-2-chlorophenyl)methyl]-4,4-dimethyl-3-isoxazolidinone was added in one portion. The reaction mixture was heated an additional 30 minutes and then 15 mL of water was added. The mixture was filtered, and the filtrate was cooled. The resultant oily suspension solidified when abraded. The solid was collected by filtration to yield, when dried, 0.87 gram of 2-[[2-chloro-4-[(2-hydroxyphenyl)methylimino]phenyl]-methyl]-4,4-dimethyl-3-isoxazolidinone; m.p. 105°–107° C.

The nmr spectrum was consistent with the proposed structure.

EXAMPLE 6

Synthesis of
2-[[2-chloro-4-[(thien-2-yl)-methylimino]phenyl]methyl]-4,4-dimethyl-3-isoxazolidinone (Compound 74)

This compound was prepared in a manner analogous to that of Example 5, using 1.28 grams (0.005 mole) of 2-[(4-amino-2-chlorophenyl)methyl]-4,4-dimethyl-3-isoxazolidinone and 0.56 gram (0.005 mole) of thiophene-2-carboxaldehyde in 25 mL of ethanol. The reaction mixture was concentrated under reduced pressure to a residual oil. The oil was dissolved in anhydrous diethyl ether and was dried for two hours with magnesium sulfate. The mixture was filtered, and the filtrate was concentrated under reduced pressure to yield 1.46 grams of 2-[[2-chloro-4-[(thien-2-yl)methylimino]-phenyl]-methyl]-4,4-dimethyl-3-isoxazolidinone as an oil.

The IR and nmr spectra were consistent with the proposed structure.

EXAMPLE 7

Synthesis of
2-[[2-chloro-4-(phthalidylidenylamino)phenyl]methyl]-4,4-dimethyl-3-isoxazolidinone (Compound 75)

A solution of 2.45 grams (0.006 mole) of 2-[[2-chloro-4-[(2-carboxyphenyl)carbonylamino]phenyl]methyl]-4,4-dimethyl-3-isoxazolidinone (prepared as in Example 2) in 35 mL of dioxane was stirred, and 2 mL of triethylamine was added. Three mL of trifluoroacetic anhydride was then added portionwise. Upon completion of addition the reaction mixture was stirred at ambient temperature for one hour, and an additional 1 mL each of triethylamine and trifluoroacetic anhydride were added. The reaction mixture was stirred for an additional one hour and then was allowed to stand for 16 hours. The reaction mixture was poured into ice-water, and the mixture was extracted with methylene chloride. The combined extracts were washed with a saturated aqueous sodium chloride solution and were dried with magnesium sulfate. The mixture was filtered, and the filtrate was concentrated under reduced pressure to a residual oil. The oil, which solidified to a semi-solid, was triturated with petroleum ether containing a small amount of ethyl acetate. The solvent was decanted from the semi-solid, and the semi-solid was dissolved in 15 mL of warm acetonitrile. The solution was filtered, allowed to cool to ambient temperature, and then placed in a refrigerator where it stood for 16 hours. The resultant solid precipitate was collected by filtration and was dried to yield 0.72 gram of 2-[[2-chloro-4-(phthalidylidenylamino)phenyl]methyl]-4,4-dimethyl-3-isoxazolidinone; m.p. 122°–126° C.

The nmr spectrum was consistent with the proposed structure.

EXAMPLE 8

Syntheses of 2-[[2chloro-4-(3,4,5,6-tetrahydrophthalimido)phenyl]methyl]-4,4-dimethyl-3-isoxazolidinone (Compound 88)

A solution of 2.0 grams (0.008 mole) of 2-[(4-amino-2-chlorophenyl)methyl]-4,4-dimethyl-3-isoxazolidinone and 1.2 grams (0.008 mole) of 3,4,5,6-tetrahydrophthalic anhydride in 20 mL of acetic acid was stirred at ambient temperature for four hours and then was heated under reflux for six hours. The cooled reaction mixture was poured into 300 mL of methylene chloride and was washed in turn with two 100 mL portions of water, two 50 mL portions of a saturated aqueous sodium bicarbonate solution, and one 50 mL portion of water. The organic layer was dried with magnesium sulfate and was filtered. The filtrate was concentrated under reduced pressure to a residual oil. The oil was subjected to column chromatography on silica gel. Elution was accomplished with 1:1 ethyl acetate:heptane. The appropriate fractions were combined and concentrated under reduced pressure to yield 2.6 grams of 2-[[2-chloro-4-(3,4,5,6-tetrahydrophthalimido)phenyl]methyl]-4,4-dimethyl-3-isoxazolidinone; m.p. 102°–104° C.

The nmr spectrum was consistent with the proposed structure.

EXAMPLE 9

Synthesis of 2-[(2-chloro-4-phthalimidophenyl)-methyl]-4,4-dimethyl-3-isoxazolidinone (Compound 101)

Step A:

Synthesis of phthalic acid, mono-methyl ester as an intermediate

Under a nitrogen atmosphere, a mixture of 75.0 grams (0.506 mole) of phthalic anhydride in 120.0 grams (3.75 moles) of methanol was stirred and heated under reflux for 30 minutes. During this time a complete solution was attained. The reaction mixture was concentrated under reduced pressure to a residual oil. The oil was placed in a refrigerator where it solidified to yield when dried, 93.0 grams of phthalic acid, mono-methyl ester; m.p. 80°–81.5° C.

The IR and nmr spectra were consistent with the proposed structure.

Step B:

Synthesis of phthaloyl chloride, methyl ester as an intermediate

Thionyl chloride, 150 ml, was stirred, and 10.0 grams (0.056 mole) of phthalic acid, methyl ester was added portionwise. Upon completion of addition the reaction mixture was warmed to 35° C. where it was stirred for four hours and then was heated to reflux where it was stirred for two hours. The reaction mixture was concentrated under reduced pressure to yield 11.9 grams of phthaloyl chloride methyl ester.

The IR spectrum was consistent with the proposed structure.

Step C:

Synthesis of 2-[(2-chloro-4-4-phthalimidophenyl)methyl]-4,4-dimethyl-3-isoxazolidinone (Compound 101)

A solution of 3.0 grams (0.012 mole) of 2-[(4-amino-2-chlorophenyl)methyl]-4,4-dimethyl-3-isoxazolidinone in 50 mL of methylene chloride was stirred, and 2.4 grams (0.024 mole) of triethylamine was added in one portion. A solution of 2.5 grams (0.012 mole) of phthaloyl chloride methyl ester in 20 mL of methylene chloride was then added dropwise. Upon completion of addition the reaction mixture was stirred at ambient temperature for 60 hours. The reaction mixture was washed with three 25 mL portions of water and was dried with magnesium sulfate. The mixture was filtered, and the filtrate was concentrated under reduced pressure to a residual oil. The oil, which solidified on standing, was recrystallized from ethyl acetate-hexane to yield 2.7 grams of 2-[(2-chloro-4-phthalimidophenyl)methyl]-4,4-dimethyl-3-isoxazolidinone; m.p. 141°–145° C.

The nmr spectrum was consistent with the proposed structure.

EXAMPLE 10

Synthesis of 2-[[2-chloro-4-(pyrrolo[3,4-b]pyridine-5,7-dione-6-yl)phenyl]methyl]-4,4-dimethyl-3-isoxazolidinone (Compound 121)

Using a method analogous to that of M. P. Cava et al., supra, a solution of 5.0 grams (0.061 mole) of sodium acetate in 50 mL of acetic anhydride was stirred while heating with a steam bath, and 1.5 grams (0.004 mole) of 2-[[2-chloro-4-[(3-carboxy-2-pyridinyl)carbonylamino]phenyl]methyl]-4,4-dimethyl-3-isoxazolidinone was added in one portion. Upon completion of addition the reaction mixture was heated with the steam bath for an additional 30 minutes. The reaction mixture was poured into 500 mL of ice-water, and the resultant solid was collected by filtration. The solid was recrystallized from acetone-water to yield 0.45 gram of 2-[[2-chloro-4-(pyrrolo[3,4-b]pyridine-5,7-dione-6-yl)phenyl]-methyl]-4,4-dimethyl-3-isoxazolidinone; m.p. 139°–141° C.

EXAMPLE 11

Synthesis of 2-[[4-[(1H-2-benzopyran-1-one-3-yl)-amino]phenyl]methyl]-4,4-dimethyl-3-isoxazolidinone (Compound 67)

Step A:

Synthesis of 2-[[4-[(2-carboxyphenylmethyl)carbonylamino]phenyl]methyl]-4,4-dimethyl-3-isoxazolidinone (Compound 59)

This compound was prepared and isolated in a manner analogous to that of Example 1, Step C, and Example 3, respectively, using 1.5 grams (0.007 mole) of 2-[(4-aminophenyl)methyl]-4,4-dimethyl-3-isoxazolidinone (prepared as in Example 13, Step B), 1.1 grams (0.007 mole) of homophthalic anhydride in 150 mL of tetrahydrofuran. The yield of 2-[[4-[(2-carboxyphenylmethyl)carbonylamino]phenyl]methyl]-4,4-dimethyl-3-isoxazolidinone was 1.1 gram; m.p. 164°-166° C.

Step B:

Synthesis of 2-[[4-[(1H-2-benzopyran-1-one-3-yl)amino]phenyl]methyl]-4,4-dimethyl-3-isoxazolidinone (Compound 67)

A solution of 0.57 gram (0.0015 mole) of 2-[[4-[(2-carboxyphenylmethyl)carbonylamino]phenyl]methyl]-4,4-dimethyl-3-isoxazolidinone in 100 mL of toluene was cooled in an ice bath, and, with stirring, 0.33 gram (0.0016 mole) of dicyclohexylcarbodiimide was added in one portion. Upon completion of addition the reaction mixture was allowed to warm to ambient temperature where it was stirred for 16 hours. The resultant solid was collected by filtration to yield 0.60 gram of 2-[[4-[(1H-2-benzopyran-1-one-3-yl)amino]phenyl]methyl]-4,4-dimethyl-3-isoxazolidinone; m.p. 175°-177° C.

The nmr spectrum was consistent with the proposed structure.

EXAMPLE 12

Synthesis of 2-[(4-amino-2-bromophenyl)methyl]-4,4-dimethyl-3-isoxazolidinone Step A:

Synthesis of 2-[(2-bromo-4-nitrophenyl)-methyl]-4,4-dimethyl-3-isoxazolidinone as an intermediate This compound was prepared and isolated by methods described in Example 1, Step C of U.S. Pat. No. 4,552,585 and Example 11, Step A above using 35.1 grams (0.305 mole) of 4,4-dimethyl-3-isoxazolidinone, 90.0 grams (0.305 mole) of 2-bromo-4-nitrobenzyl bromide, 42.2 grams (0.305 mole) of potassium carbonate, and 0.8 gram (0.0031 mole) of 1,4,7,10,13,16-hexaoxacyclooctadecane in 1000 mL of acetonitrile. The yield of 2-[(2-bromo-4-nitrophenyl)-methyl]-4,4-dimethyl-3-isoxazolidinone was 50.0 grams as a solid.

Step B:

Synthesis of 2-[(4-amino-2-bromophenyl)-methyl]-4,4-dimethyl-3-isoxazolidinone This compound was prepared and isolated in a manner analogous to that of Example 11, Step B, using 3.0 grams (0.091 mole) of 2-[(2-bromo-4-nitrophenyl)methyl]-4,4-dimethyl-3-isoxazolidinone, 0.3 gram of platinum oxide, and hydrogen gas in 150 mL of methanol. The yield of 2-[(4-amino-2-bromophenyl)methyl]-4,4-dimethyl-3-isoxazolidinone was 0.5 gram; m.p. 109°-111° C.

The nmr spectrum was consistent with the proposed structure.

EXAMPLE 13

Synthesis of 2-[[2-bromo-4-[(2-carboxycyclohex-1-enyl)carbonylamino]phenyl]methyl]-4,4-dimethyl-3-isoxazolidinone (Compound 22)

This compound was prepared in a manner analogous to that of Example 1, Step C, using 2.0 grams (0.0067 mole) of 2-[(4-amino-2-bromophenyl)methyl]-3-isoxazolidinone (prepared as in Example 13, Step B) and 1.0 gram (0.0067 mole) of 3,4,5,6-tetrahydrophthalic anhydride in 50 mL of tetrahydrofuran. The reaction mixture was concentrated under reduced pressure to a residual solid. The solid was recrystallized from acetone-water to yield 0.75 gram of 2-[[2-bromo-4-[(2-carboxycyclohex-1-enyl)-carbonylamino]phenyl]methyl]-4,4-dimethyl-3-isoxazolidinone; m.p. 149°-151° C. The nmr spectrum was consistent with the proposed structure.

EXAMPLE 14

Synthesis of 2-[[2-bromo-4-[(2-carboxyphenyl)-carbonylamino]-phenyl]methyl]-4,4-dimethyl-3-isoxazolidinone (Compound 36)

This compound was prepared in a manner analogous to that of Example 1, Step C, using 2.0 grams (0.0067 mole) of 2-[(4-amino-2-bromophenyl)methyl]-4,4-dimethyl-3-isoxazolidinone and 1.0 gram (0.0067 mole) of phthalic anhydride in 50 ml of tetrahydrofuran. The reaction mixture was concentrated under reduced pressure to a residual solid. The solid was recrystallized from ethyl acetate-hexane to yield 2.8 grams of 2-[[2-bromo-4-[(2-carboxyphenyl)carbonylamino]phenyl]methyl]-4,4-dimethyl-3-isoxazolidinone, m.p. 177° C., dec.

The nmr spectrum was consistent with the proposed structure.

EXAMPLE 15

Synthesis of 2-[(2-bromo-4-phthalimidophenyl)-methyl]-4,4-dimethyl-3-isoxazolidinone (Compound 102)

This compound was prepared in a manner analogous to that of Example 10, using 2.0 grams (0.004 mole) of 2-[[2-bromo-4-[(2-carboxyphenyl)carbonylamino]-phenyl]-methyl]-4,4-dimethyl-3-isoxazolidinone and 5.0 grams (0.061 mole) of sodium acetate in 50 mL of acetic anhydride. The solid was recrystallized from ethyl acetatehexane to yield 2-[(2-bromo-4-phthalimidophenyl)methyl]-4,4-dimethyl-3-isoxazolidinone; m.p. 158°-159° C.

The nmr spectrum was consistent with the proposed structure.

EXAMPLE 16

Synthesis of 2-[(2,3-dichloro-4-phthalimidophenyl)-methyl]-4,4-dimethyl-3-isoxazolidinone (Compound 105)

Step A:

Synthesis of N-(2,3-dichloro-4-methylphenyl)benzoic acid-2-carboxamide as an intermediate This compound was prepared in a manner analogous to that of Example 1, Step C, using 4.0 grams (0.023 mole) of 2,3-dichloro-4-methylaniline and 6.8 grams (0.046 mole) of phthalic anhydride in 300 ml of tetrahydrofuran. The reaction mixture was concentrated under reduced pressure to a residual solid. The solid was recrystallized from methanol-water to yield 3.5 grams of N-(2,3-dichloro-4-methylphenyl)benzoic acid-2-carboxamide.

The nmr spectrum was consistent with the proposed structure.

Step B:

Synthesis of N-(2,3-dichloro-4-methylphenyl)phthalimide as an intermediate

A solution of 6.1 grams (0.019 mole) of N-(2,3-dichloro-4-methylphenyl)benzoic acid-2-carboxamide and 20 ml of concentrated sulfuric acid in 150 ml of methanol was heated under reflux for two hours. The reaction mixture was concentrated under reduced pressure to a residue. The residue was poured into 500 ml of water, and the resultant solid was collected by filtration to yield 4.7 grams of N-(2,3-dichloro-4-methylphenyl)-phthalimide; m.p. 109° C. The nmr spectrum was consistent with the proposed structure.

Step C:

Synthesis of N-(4-bromomethyl-2,3-dichlorophenyl)phthalimide as an intermediate A solution of 4.0 grams (0.013 mole) of N-(2,3-dichloro-4-methylphenyl)phthalimide, 2.3 grams (0.013 mole) of N-bromosuccinimide and 0.3 gram of benzoyl peroxide in 200 ml of carbon tetrachloride was heated under reflux for 22 hours. The cooled reaction mixture was poured into 500 ml of ethyl acetate. The solution was washed with three 100 ml portions of water. The organic layer was dried with magnesium sulfate and was filtered. The filtrate was concentrated under reduced pressure to a residue. The residue was subjected to column chromatography on silica gel. Elution was accomplished using ethyl acetate:heptane (1:4). The appropriate fractions were combined and concentrated under reduced pressure to yield 4.4 grams of N-(4-bromomethyl-2,3-dichlorophenyl)phthalimide as a solid.

The nmr spectrum was consistent with the proposed structure.

Step D:

Synthesis of 2-[(2,3-dichloro-4-phthalimidophenyl)methyl]-4,4-dimethyl-3-isoxazolidinone (Compound 105)

This compound was prepared by methods described in Example 1, Step C, of U.S. Pat. No. 4,552,585 using 1.3 grams (0.011 mole) of 4,4-dimethyl-3-isoxazolidinone, 4.4 grams (0.011 mole) of N-(4-bromomethyl-2,3-dichlorophenyl)phthalimide, 1.6 grams (0.011 mole) of potassium carbonate, and 0.1 gram (0.0004 mole) of 1,4,7,10,13,16-hexaoxacyclooctadecane in 100 ml of acetonitrile. The reaction mixture was poured into 300 ml of ethyl acetate and was washed with three 50 ml portions of water. The organic layer was dried with magnesium sulfate and filtered. The filtrate was concentrated under reduced pressure to a residue. The residue was subjected to column chromatography on silica gel. Elution was accomplished using ethyl acetate:heptane (1:1). The appropriate fractions were combined and concentrated under reduced pressure to yield 2.1 grams of 2-[2,3-dichloro-4-phthalimidophenyl)methyl]-4,4-dimethyl-3-isoxazolidinone; m.p. 160°-162° C. The nmr spectrum was consistent with the proposed structure.

The plant growth and development modifiers of the present invention were investigated for activity in preemergence and postemergence tests according to the following procedure:

Flats were filled with a steam sterilized sandy loam soil. Seeds of the following test plant species were planted in furrows: cotton (*Gossypium hirsutum*), lima bean (*Phaseolus limensis*), field corn (*Zea mays L.*), soybean (*Glycine max*), wheat (*Triticum aestivum*), barnyardgrass (*Echinochloa crus-galli*), johnsongrass (*Sorghum halepense*), pitted morningglory (*Ipomoea lacunosa*), velvetleaf (*Abutilon theophrasti*), field bindweed (*Convolvulus arvensis*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for preemergence tests was watered and the soil evenly drenched with the water-acetone solution of test chemical. The treated flat was placed in a greenhouse where it was watered regularly at the soil surface for a period of 13 days. The effect of the test chemical was then recorded.

A flat for postemergence test was placed in a greenhouse for an 8 to 10 day growing period. The test solution was then hand-sprayed onto the foliage of the emerged test plants. After spraying, the foliage of the test plants was kept dry for 24 hours after which time regular watering was resumed for a period of 13 days. The effect of the test chemical was then recorded.

In the tests the plants were examined for herbicidal activity and morphological responses indicative of plant regulator activity. Virtually all compounds displayed some herbicidal activity at high application rates, i.e., rates of about 8 kg/ha.

Morphological responses that are indicative of plant regulator activity and that were observed when plants were treated with compounds of this invention include:

Stunting (Activity B) is manifested by treated plants which do not grow as tall as untreated plants. This plant regulator effect can be utilized with grasses in the maintenance of lawns, golf courses, and highway rights of way by reducing the frequency of mowings. Cereal and broadleaf crops such as wheat, cotton, and soybeans that have been treated with a chemical which causes stunting develop shorter, thicker stems which resist lodging, thus allowing more complete harvesting of the crop. Stem growth in treated fruit trees may be reduced, resulting in reduced need for pruning and a concomitant reduction in time expended in trimming the trees.

Desiccation (Activity C) is the reduction of moisture content of treated plants. This effect can be utilized to reduce the preharvest moisture content of cereals, e.g., wheat, or broadleaf crops, e.g., sunflower or soybeans. Harvesting may be significantly aided by desiccation which results in the loss of foliage. Crops in which the loss of foliage is desirable before harvesting include cotton, soybeans, peanuts, and potatoes.

Axillary growth stimulation (Activity D) is manifested by increased branching, particularly in the angle between a leaf or branch and the axis from which it originates. In cereals such as wheat axillary growth stimulation leads to multiple stems known as tillers. In soybeans axillary stimulation at flowering can result in increased pod set. In both cereals and soybeans an increased yield may result from the treatment.

Nastic response (Activity E) is manifested by the twisting and bending of plants or parts thereof which is indicative of a hormonal change or disruption. A natural and useful nastic response is the curling of a tendril or a stem around a support, e.g., in peas or pole beans.

Defoliation (Activity H) is the chemically induced loss or removal of plant foliage. This is usually done just prior to harvesting cotton to avoid foliage stains on the crop. Harvesting of soybeans, peanuts, and potatoes is also facilitated by prior defoliation.

Intumescence (Activity J) is manifested by the formation of abnormal swellings and is indicative of a disruption of the hormonal balance required for normal growth. Intumescence-causing agents can promote growth of tissue, such as tobacco callus.

Negative root geotropism (Activity M) is the upward growth of roots out of the soil and is indicative of a disruption of the plant's normal hormonal balance. This effect can be correlated with an increase in the number of pods on treated soybean plants.

Deeper green lower leaves (Activity P) suggests delay of senescence, increased chlorophyll production, or chlorophyll retention. These phenomena are indicative of greater photosynthesis which may increase yield in crops such as soybeans.

Leaf Alteration (Activity Q) indicates disruption in the plant's hormonal balance. Leaves of plants may be altered to allow better utilization of sunlight which, in turn, may enhance plant growth.

The responses indicating plant regulatory activity in preemergence and postemergence applications are set forth in Table II.

TABLE II

| Cmpd. No. | Test Type[1] | Plant Growth Regulating Morphological Response[2] | | | | |
|---|---|---|---|---|---|---|
| | | Lima Bean | Soybean | Cotton | Corn | Wheat |
| 10 | PRE | * | BE | — | B | — |
| | POST | * | BDE | — | — | — |
| 11 | PRE | * | BDEM | M | M | EM |
| | POST | * | BDE | — | — | — |
| 12 | PRE | * | BDE | M | BM | M |
| | POST | * | BD | — | — | — |
| 13 | PRE | * | BDE | — | — | — |
| | POST | * | BDE | — | — | — |
| 14 | PRE | * | BDM | M | M | E |
| | POST | * | — | — | M | — |
| 15 | PRE | * | B | — | — | E |
| | POST | * | BDP | BE | — | BE |
| 16 | PRE | * | BE | B | M | E |
| | POST | * | BDMP | M | M | BE |
| 17 | PRE | * | BD | — | M | — |
| | POST | * | BD | E | — | — |
| 18 | PRE | * | BE | — | M | E |
| | POST | * | BDE | — | — | E |
| 19 | PRE | * | B | B | B | B |
| | POST | * | BD | — | — | — |
| 20 | PRE | * | B | — | B | — |
| | POST | * | D | — | — | — |
| 21 | PRE | * | BD | BEM | BM | E |
| | POST | * | BDEM | EM | M | M |
| 22 | PRE | * | BE | B | BM | BE |
| | POST | * | BEMP | BEM | M | — |
| 23 | PRE | * | B | — | — | B |
| | POST | * | BDP | — | — | — |
| 24 | PRE | * | BE | — | — | B |
| | POST | * | BDEM | E | M | EM |
| 25 | PRE | * | BM | BEM | M | E |
| | POST | * | — | — | — | — |
| 26 | PRE | * | BEM | BM | BEM | BE |
| | POST | * | BDEMP | — | M | — |
| 27 | PRE | * | BDEM | — | M | E |
| | POST | * | BDEM | M | M | M |
| 28 | PRE | * | — | — | M | — |
| | POST | * | — | — | — | — |
| 29 | PRE | * | DEM | M | M | M |
| | POST | * | D | — | — | — |
| 30 | PRE | * | BDE | B | — | — |
| | POST | * | BDE | — | B | — |
| 31 | PRE | * | BE | — | — | — |
| | POST | * | BDEM | M | BM | M |
| 32 | PRE | * | BDEM | BM | M | — |
| | POST | * | BCDE | BC | — | C |
| 34 | PRE | * | — | BE | BE | BPE |
| | POST | * | BD | BEH | M | BE |
| 35 | PRE | B | BE | * | BE | BE |
| | POST | B | BD | * | — | — |
| 36 | PRE | * | — | BE | B | BE |
| | POST | * | BP | BE | B | — |
| 37 | PRE | * | BE | — | BE | BE |
| | POST | * | BD | BE | BEM | BE |

TABLE II-continued

| Cmpd. No. | Test Type[1] | Plant Growth Regulating Morphological Response[2] | | | | |
|---|---|---|---|---|---|---|
| | | Lima Bean | Soybean | Cotton | Corn | Wheat |
| 38 | PRE | * | — | — | — | — |
| | POST | * | BD | BE | BE | — |
| 39 | PRE | * | BE | B | BE | BE |
| | POST | * | BDEMP | BEM | M | — |
| 40 | PRE | * | B | BE | BE | BE |
| | POST | * | BE | BE | EM | EM |
| 41 | PRE | * | BE | BE | BEM | BE |
| | POST | * | BDE | BE | BEM | E |
| 42 | PRE | * | — | BE | BE | BE |
| | POST | * | BEMP | EM | M | M |
| 43 | PRE | * | BP | B | BE | BE |
| | POST | * | BDEMP | — | M | — |
| 44 | PRE | * | BE | BE | BE | BE |
| | POST | * | BDE | BE | BM | — |
| 45 | PRE | * | — | — | EM | E |
| | POST | * | BDEMP | BEMQ | BM | M |
| 46 | PRE | * | M | M | M | M |
| | POST | * | DE | B | — | — |
| 47 | PRE | * | — | — | — | — |
| | POST | * | DE | E | — | — |
| 48 | PRE | * | BG | BG | BM | BE |
| | POST | * | BD | — | B | B |
| 49 | PRE | * | BE | BE | BEP | BE |
| | POST | * | BDE | E | BEMP | E |
| 50 | PRE | * | BE | B | — | BE |
| | POST | * | BDEM | E | M | M |
| 51 | PRE | * | BDE | — | — | — |
| | POST | * | BDE | — | B | — |
| 52 | PRE | * | BDEM | BM | M | — |
| | POST | * | BD | — | — | — |
| 53 | PRE | * | M | — | M | — |
| | POST | * | BDE | — | M | — |
| 54 | PRE | * | BDE | BEM | BE | E |
| | POST | * | BDM | — | M | M |
| 55 | PRE | BEM | BM | * | BM | EM |
| | POST | BDE | BDM | * | M | — |
| 56 | PRE | * | E | M | M | M |
| | POST | * | BCDE | — | — | — |
| 57 | PRE | * | BDE | — | — | — |
| | POST | * | CDEM | — | C | C |
| 58 | PRE | * | — | M | — | — |
| | POST | * | D | — | — | — |
| 59 | PRE | * | BM | BE | M | BE |
| | POST | * | BD | — | BEM | BE |
| 60 | PRE | * | — | BE | BE | BE |
| | POST | * | BDM | BEM | M | — |
| 61 | PRE | * | — | — | B | BE |
| | POST | * | BD | — | B | B |
| 63 | PRE | * | BDE | BE | E | BE |
| | POST | * | — | — | — | — |
| 64 | PRE | * | BE | M | M | BE |
| | POST | * | — | — | — | — |
| 65 | PRE | * | BEM | M | M | BM |
| | POST | * | B | — | B | B |
| 66 | PRE | * | D | — | — | — |
| | POST | * | — | — | — | — |
| 67 | PRE | * | BM | BM | EM | BE |
| | POST | * | BDMP | BM | BM | BM |
| 68 | PRE | * | M | M | — | M |
| | POST | * | — | — | — | — |
| 71 | PRE | * | BE | B | B | B |
| | POST | * | BDE | — | — | — |
| 72 | PRE | * | BDM | — | — | — |
| | POST | * | BD | E | — | — |
| 73 | PRE | * | BE | — | — | — |
| | POST | * | BDP | B | — | — |
| 74 | PRE | * | BD | — | B | — |
| | POST | * | BD | E | B | B |
| 75 | PRE | * | BDE | BE | BE | BD |
| | POST | * | BCDEM | BCM | BCM | CM |
| 76 | PRE | * | BEMJ | — | M | — |
| | POST | * | BDEP | B | — | — |
| 77 | PRE | * | BE | B | B | BE |
| | POST | * | BE | EM | M | EM |
| 78 | PRE | * | B | B | BE | BE |
| | POST | * | BDEMP | BEMQ | M | EM |
| 79 | PRE | * | B | B | BMP | BE |

TABLE II-continued

| Cmpd. No. | Test Type[1] | Lima Bean | Soybean | Cotton | Corn | Wheat |
|---|---|---|---|---|---|---|
|  | POST | * | BDE | BE | BM | — |
| 80 | PRE | * | BE | B | — | E |
|  | POST | * | BDM | — | — | — |
| 81 | PRE | * | — | — | — | — |
|  | POST | * | — | — | — | — |
| 82 | PRE | * | BDMP | M | — | — |
|  | POST | * | BDE | B | B | — |
| 83 | PRE | * | BDEM | M | M | M |
|  | POST | * | BCD | C | C | — |
| 84 | PRE | * | BDE | M | BM | — |
|  | POST | * | BD | — | — | — |
| 85 | PRE | * | BDE | BE | — | — |
|  | POST | * | BCDE | C | — | C |
| 86 | PRE | * | BE | M | M | BE |
|  | POST | * | BCDEM | CM | CM | BCEM |
| 87 | PRE | * | B | — | BM | E |
|  | POST | * | BDEP | — | — | — |
| 88 | PRE | BEM | BEM | * | BEM | BEM |
|  | POST | BCDEM | BCDEM | * | CM | CM |
| 89 | PRE | * | BP | B | — | B |
|  | POST | * | BCEMP | B | M | M |
| 90 | PRE | * | BDM | — | M | BEM |
|  | POST | * | BDE | BE | M | BM |
| 91 | PRE | * | BE | BE | EM | BE |
|  | POST | * | BDE | E | EM | E |
| 92 | PRE | * | B | E | BE | E |
|  | POST | * | — | — | — | — |
| 93 | PRE | * | BP | B | — | BE |
|  | POST | * | BDMP | — | M | M |
| 94 | PRE | * | BDE | — | BE | E |
|  | POST | * | BDM | EM | M | M |
| 95 | PRE | * | — | — | M | — |
|  | POST | * | B | — | E | B |
| 96 | PRE | * | BEM | — | M | BE |
|  | POST | * | BDEM | — | M | E |
| 97 | PRE | * | — | — | — | — |
|  | POST | * | E | — | — | — |
| 98 | PRE | * | B | B | B | — |
|  | POST | * | BCD | — | B | BD |
| 99 | PRE | * | BEM | — | — | E |
|  | POST | * | BCDE | C | — | C |
| 100 | PRE | * | B | — | EM | BE |
|  | POST | * | BD | BE | EM | E |
| 101 | PRE | EHJ | BJ | * | BJ | BJ |
|  | POST | BE | BE | * | B | — |
| 102 | PRE | * | B | — | MEP | BE |
|  | POST | * | BP | BE | BM | — |
| 103 | PRE | * | BE | — | BE | BE |
|  | POST | * | BDMP | BEM | BEM | BE |
| 104 | PRE | * | BE | B | BM | BEM |
|  | POST | * | BD | B | BM | — |
| 105 | PRE | * | BDM | BEM | BEM | BEMP |
|  | POST | * | BCDEM | BCEM | BCM | CEM |
| 106 | PRE | * | BE | B | BE | BE |
|  | POST | * | BEDP | — | EM | M |
| 107 | PRE | * | BE | E | BE | B |
|  | POST | * | BDE | E | EM | BE |
| 108 | PRE | * | BDEM | BEM | M | BE |
|  | POST | * | BDE | BE | BM | EM |
| 109 | PRE | * | BDEP | B | BE | BEM |
|  | POST | * | E | — | — | — |
| 110 | PRE | * | BP | B | B | BE |
|  | POST | * | BDEMJP | E | M | EM |
| 111 | PRE | * | BDEHP | B | BEP | BE |
|  | POST | * | DE | — | — | — |
| 112 | PRE | * | E | — | M | E |
|  | POST | * | DE | B | M | — |
| 113 | PRE | * | BDM | M | M | M |
|  | POST | * | — | — | — | — |
| 114 | PRE | * | — | — | — | — |
|  | POST | * | * | * | * | * |
| 115 | PRE | * | M | — | M | — |
|  | POST | * | B | — | B | — |
| 116 | PRE | * | BE | — | BEP | BE |
|  | POST | * | BDEP | E | BM | E |
| 117 | PRE | * | EM | M | — | M |
|  | POST | * | BDM | B | BM | M |
| 118 | PRE | * | — | — | — | — |
|  | POST | * | M | — | M | M |
| 119 | PRE | * | — | — | — | — |
|  | POST | * | B | B | B | B |
| 120 | PRE | * | — | — | — | — |
|  | POST | * | — | — | — | — |
| 121 | PRE | * | BEM | — | BEM | BM |
|  | POST | * | BPEMP | EMQ | BEM | EM |
| 122 | PRE | * | M | M | M | — |
|  | POST | * | BD | BM | — | E |
| 123 | PRE | * | D | — | — | — |
|  | POST | * | D | — | — | — |
| 124 | PRE | * | M | M | M | — |
|  | POST | * | — | — | — | — |
| 125 | PRE | * | BE | BE | BE | BE |
|  | POST | * | B | B | B | — |
| 126 | PRE | * | — | — | — | — |
|  | POST | * | B | — | — | — |

*Not tested
— Did not show plant growth regulating morphological response.
[1] PRE = Preemergence, POST = Postemergence
[2] B = Stunting
C = Desiccation
D = Axillary growth stimulation
E = Nastic responses
G = Growth stimulation
H = Defoliation
J = Intumescence
M = Negative root geotropism
P = Darker green basal leaves
Q = Leaf alteration

What is claimed is:

1. A plant regulating 2-[(4-substituted phenyl)-methyl]-4,4-dimethyl-3-isoxazolidinone of the formula or an agriculturally acceptable salt thereof in which
(A)
A is hydrogen or halogen,
B is hydrogen or halogen,
or A and B together form —$C_4H_4$— bridging adjacent carbon atoms;
R is hydrogen or lower alkyl;

R1 is $\underset{\underset{O}{\|}}{C}-Y-\underset{\underset{O}{\|}}{C}-OR^2$ or $R^2$ is hydrogen, methyl diphenylmethyl or an agriculturally acceptable cation, and Y is
(a) lower alkylene or lower alkenylene which may be substituted with halogen or phenyl,
(b) ortho-cyclohexylene or ortho-cyclohexenylene which may be substituted with methyl,
(c) ortho-bicycloalkylene of 7 or 8 carbon atoms,
(d) ortho-oxabicycloalkenylene of 6 or 7 carbon atoms,
(e) ortho-phenylene which may be substituted with lower alkyl, halogen, nitro, a group of formula I

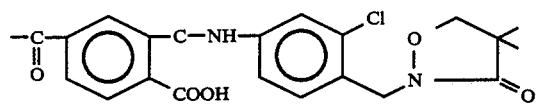

or with carboxyl and a group of formula II

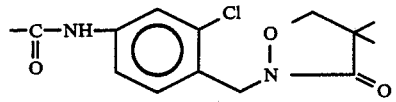

(f) ortho-naphthalene, (g) ortho-phenylmethylene, (B) A and B are as defined above and $NRR^1$ is (2-hydroxyphenyl)methylimino, (4-halo-2-hydroxyphenyl)-methylimino, (thien-2-yl)methylimino, phthalidylidenylamino, or a group of the formula

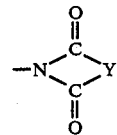

in which Y is as defined above

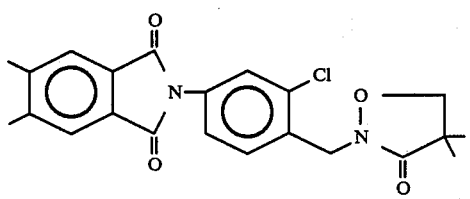

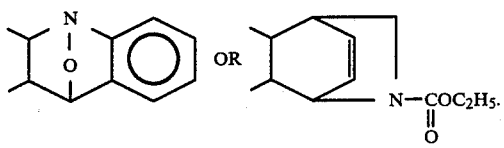

2. A plant regulating composition comprising a plant regulating amount of a compound of claim 1 in admixture with an agriculturally acceptable vehicle, adjuvant, or diluent.

3. A method for regulating growth and development of desirable agricultural crop plants which comprises applying to the plant or to site where the plant is or is about to be planted a plant regulating amount of the compound of claim 1.

* * * * *

UNITED STATES PATENT AND TRADEMARK OFFICE
CERTIFICATE OF CORRECTION

PATENT NO. : 4,892,578

DATED : January 9, 1990

INVENTOR(S) : Jun H. Chang, Jonathan S. Baum

It is certified that error appears in the above-identified patent and that said Letters Patent is hereby corrected as shown below:

Column 16, line 8, "2-[(2-chloro-4-4-phthalimidophenyl)methyl]-4,4-" sould read -- 2-[(2-chloro-4-phthalimidophenyl)methyl]-4,4- --.

Signed and Sealed this

Eleventh Day of December, 1990

Attest:

HARRY F. MANBECK, JR.

Attesting Officer

Commissioner of Patents and Trademarks